US010451593B2

(12) United States Patent
Barshad et al.

(10) Patent No.: US 10,451,593 B2
(45) Date of Patent: Oct. 22, 2019

(54) DETECTION SYSTEM AND METHOD WITH NANOSTRUCTURE FLOW CELL

(71) Applicant: AA HOLDINGS, LTD, Burlington, MA (US)

(72) Inventors: Yoav Barshad, Brookline, MA (US); Adam B. Thibault, Somerville, MA (US)

(73) Assignee: AA Holdings, Ltd., Burlington, MA (US)

( * ) Notice: Subject to any disclaimer, the term of this patent is extended or adjusted under 35 U.S.C. 154(b) by 251 days.

(21) Appl. No.: 15/669,342

(22) Filed: Aug. 4, 2017

(65) Prior Publication Data

US 2018/0128790 A1 May 10, 2018

Related U.S. Application Data

(60) Provisional application No. 62/371,044, filed on Aug. 4, 2016.

(51) Int. Cl.
*G01N 30/52* (2006.01)
*G01N 30/74* (2006.01)
(Continued)

(52) U.S. Cl.
CPC ............ *G01N 30/52* (2013.01); *G01N 21/31* (2013.01); *G01N 21/85* (2013.01);
(Continued)

(58) Field of Classification Search
CPC .... G01N 30/52; G01N 30/74; G01N 30/6095; G01N 30/8679; G01N 21/31;
(Continued)

(56) References Cited

U.S. PATENT DOCUMENTS

| | | | | | |
|---|---|---|---|---|---|
| 3,920,334 | A | * | 11/1975 | Steichen | G01N 21/645 250/343 |
| 4,044,257 | A | * | 8/1977 | Kreuzer | G01J 3/427 250/343 |
| 4,375,163 | A | * | 3/1983 | Yang | G01N 30/6078 210/198.2 |
| 4,618,769 | A | * | 10/1986 | Johnson | G01N 21/05 250/338.1 |

(Continued)

OTHER PUBLICATIONS

McKeogh, Gerard; Moisture Measurement Technologies for Natural Gas; white paper; https://www.gemeasurement.com; pp. 1-12.

*Primary Examiner* — David J Bolduc
(74) *Attorney, Agent, or Firm* — Davis, Malm & D'Agostine, P.C.; Richard L. Sampson (57) ABSTRACT

A system and method for determining concentration of a constituent of a sample fluid includes a flow cell with a light source emitting incident light to a proximal end thereof. Media disposed within the flow cell supports nanostructures that are substantially transparent in at least a portion of the incident light spectrum. The nanostructures adsorb or absorb the constituent to attain a concentration that is a multiple of the concentration of the constituent in the sample fluid. A sensor detects transmitted light exiting from the media, and generates outputs corresponding to a spectrum of the transmitted light. A processor captures the sensor outputs and compares the incident light spectrum to the transmitted light spectrum to generate an absorbance spectrum. The absorbance spectrum is used to calculate the concentration in the nanostructures, which is then used with the predetermined multiple to calculate the sample concentration.

20 Claims, 3 Drawing Sheets

(51) Int. Cl.
*G01N 30/86* (2006.01)
*G01N 30/60* (2006.01)
*G01N 21/31* (2006.01)
*G01N 21/85* (2006.01)
*G01N 21/81* (2006.01)
*G01N 21/77* (2006.01)

(52) U.S. Cl.
CPC ......... *G01N 30/6095* (2013.01); *G01N 30/74* (2013.01); *G01N 30/8679* (2013.01); *G01N 21/81* (2013.01); *G01N 2021/7723* (2013.01); *G01N 2021/7726* (2013.01); *G01N 2030/524* (2013.01)

(58) Field of Classification Search
CPC ............... G01N 21/81; G01N 21/85; G01N 2021/7723; G01N 2021/7726; G01N 2030/524
See application file for complete search history.

(56) References Cited

U.S. PATENT DOCUMENTS

| | | | | |
|---|---|---|---|---|
| 4,908,676 A * | 3/1990 | Bedell | G01N 21/85 | 250/565 |
| 4,988,446 A * | 1/1991 | Haberman | C10G 11/187 | 210/198.2 |
| 5,076,909 A * | 12/1991 | Overfield | C10G 11/187 | 208/177 |
| 5,250,186 A * | 10/1993 | Dollinger | G01N 15/0205 | 210/198.2 |
| 5,407,638 A * | 4/1995 | Wang | G01N 21/05 | 250/576 |
| 5,408,326 A * | 4/1995 | Wang | G01N 21/255 | 250/576 |
| 5,444,807 A * | 8/1995 | Liu | G01N 30/74 | 204/452 |
| 5,917,606 A * | 6/1999 | Kaltenbach | G01N 21/05 | 204/452 |
| 6,108,083 A * | 8/2000 | Machler | G01J 3/02 | 356/246 |
| 6,319,469 B1 * | 11/2001 | Mian | B01F 13/0059 | 422/63 |
| 6,342,948 B1 * | 1/2002 | Gilby | G01N 21/0303 | 356/246 |
| 6,344,172 B1 * | 2/2002 | Afeyan | G01N 30/461 | 210/198.2 |
| 6,629,039 B1 * | 9/2003 | Wang | G01N 30/8689 | 702/22 |
| 2002/0024662 A1 | 2/2002 | Ueno | G01N 21/0332 | 356/246 |
| 2004/0200776 A1 * | 10/2004 | Ivanov | B01J 20/26 | 210/656 |
| 2005/0023445 A1 * | 2/2005 | Horn | G01N 21/645 | 250/214 R |
| 2005/0078308 A1 * | 4/2005 | Gilby | G01N 21/0303 | 356/246 |
| 2005/0221503 A1 * | 10/2005 | Drachev | G01N 21/658 | 436/518 |
| 2005/0257885 A1 * | 11/2005 | Hobbs | G01N 21/05 | 156/293 |
| 2006/0082778 A1 * | 4/2006 | Paldus | G01N 21/39 | 356/437 |
| 2006/0084180 A1 * | 4/2006 | Paldus | G01N 21/3504 | 436/171 |
| 2006/0181710 A1 * | 8/2006 | Kachanov | G01N 21/39 | 356/437 |
| 2006/0263777 A1 * | 11/2006 | Tong | G01J 3/42 | 435/6.12 |
| 2007/0076204 A1 * | 4/2007 | Mueller | G01N 21/0303 | 356/369 |
| 2007/0145275 A1 * | 6/2007 | Wong | G01N 21/3504 | 250/339.13 |
| 2007/0259440 A1 * | 11/2007 | Zhou | G01N 21/3504 | 436/141 |
| 2007/0273882 A1 * | 11/2007 | Smith | G01N 21/39 | 356/437 |
| 2007/0291255 A1 * | 12/2007 | Larsen | G01J 3/02 | 356/73 |
| 2008/0035848 A1 * | 2/2008 | Wong | G01J 3/02 | 250/345 |
| 2008/0304048 A1 * | 12/2008 | Tormod | G01N 21/05 | 356/51 |
| 2009/0166560 A1 * | 7/2009 | Dai | B82Y 5/00 | 250/492.1 |
| 2009/0308811 A1 * | 12/2009 | Tepper | B01J 20/282 | 210/656 |
| 2009/0325318 A1 * | 12/2009 | Carron | G01N 33/54326 | 436/526 |
| 2010/0262034 A1 * | 10/2010 | Kawata | A61B 5/097 | 600/532 |
| 2010/0285490 A1 * | 11/2010 | Dees | G01N 33/54373 | 435/7.1 |
| 2011/0014724 A1 * | 1/2011 | Sim | G01N 33/54346 | 436/525 |
| 2011/0154806 A1 * | 6/2011 | Hoyte | F01N 3/208 | 60/276 |
| 2011/0271838 A1 * | 11/2011 | Mitra | B01D 53/0407 | 96/102 |
| 2012/0127469 A1 * | 5/2012 | Tsukada | G01N 30/74 | 356/436 |
| 2012/0184046 A1 * | 7/2012 | Atkin | B01L 3/502707 | 436/161 |
| 2012/0262718 A1 * | 10/2012 | Yamada | G01N 29/022 | 356/436 |
| 2013/0135617 A1 * | 5/2013 | Pris | G01N 21/554 | 356/326 |
| 2013/0168543 A1 * | 7/2013 | Barron | G01N 30/74 | 250/259 |
| 2013/0243874 A1 * | 9/2013 | Sun | B82Y 30/00 | 424/497 |
| 2014/0030696 A1 * | 1/2014 | Luscher | G01N 15/1404 | 435/3 |
| 2014/0260535 A1 * | 9/2014 | McGill | G01N 30/74 | 73/23.37 |
| 2014/0333933 A1 * | 11/2014 | James | G01N 33/0045 | 356/432 |
| 2014/0370607 A1 * | 12/2014 | Dimick | G01N 21/85 | 436/37 |
| 2015/0052984 A1 * | 2/2015 | Barka | G01J 3/28 | 73/61.48 |
| 2015/0153272 A1 * | 6/2015 | Ehring | G01N 30/74 | 250/373 |
| 2015/0260693 A1 * | 9/2015 | DeMarco | G01N 30/26 | 356/72 |
| 2015/0330887 A1 * | 11/2015 | Shin | B01L 3/50273 | 73/61.55 |
| 2015/0338348 A1 * | 11/2015 | Schultz | G01N 15/1429 | 356/301 |
| 2016/0047738 A1 * | 2/2016 | Charlton | G01N 30/74 | 356/440 |
| 2016/0054275 A1 * | 2/2016 | Andrews | G01N 21/274 | 356/440 |
| 2016/0084757 A1 * | 3/2016 | Miron | G01N 21/39 | 356/437 |
| 2016/0109369 A1 * | 4/2016 | Ukon | G01N 30/74 | 356/301 |
| 2016/0132617 A1 * | 5/2016 | Liu | G06F 17/5009 | 703/2 |
| 2016/0282318 A1 * | 9/2016 | Malmquist | G01N 30/8624 | |
| 2017/0059477 A1 * | 3/2017 | Feitisch | G01N 21/274 | |
| 2017/0266654 A1 * | 9/2017 | Sanroma | B01L 3/502 | |
| 2018/0024051 A1 * | 1/2018 | Zemek | G01N 21/01 | 356/409 |

* cited by examiner

DETECTION SYSTEM AND METHOD WITH NANOSTRUCTURE FLOW CELL

This application claims the benefit of U.S. Provisional Patent Application Ser. No. 62/371,044, entitled Moisture Sensor, filed on Aug. 4, 2016, the contents of which are incorporated herein by reference in their entirety for all purposes.

BACKGROUND

Technical Field

This invention relates to property detection, and more particularly to a system and method for detecting constituents of process fluids.

Background Information

Throughout this application, various publications, patents and published patent applications are referred to by an identifying citation. The disclosures of the publications, patents and published patent applications referenced in this application are hereby incorporated by reference into the present disclosure.

Detection of components such as moisture and other constituents within fluids (liquids and gases) is a substantial challenge. It is desirable, for example, to detect the presence of moisture within natural gas. Other examples include the detection of various constituents of hydrocarbon fluids for blending analysis and/or to detect the presence of specific deleterious constituents such as hydrogen sulfide, etc.

Many approaches exist for such detection of moisture and other constituents, many of which are optical in nature. Such detection, however, is particularly challenging when concentrations of constituents of interest are relatively low. Thus, a need exists for an improved system and method capable of detecting relatively low concentrations of constituents in sample fluids.

SUMMARY

In one aspect of the present invention, a system is provided for optically determining the concentration of a constituent of a sample fluid in real time, the system includes a flow cell configured to convey the sample fluid therethrough from a proximal end to a distal end, and a light source disposed in optical communication with the proximal end of the flow cell, the light source configured to emit incident light of an incident light spectrum into the flow cell. Media within the flow cell supports nanostructures that are substantially transparent in at least a portion of the incident light spectrum. The nanostructures are configured to adsorb or absorb the constituent to attain a concentration that is a predetermined multiple of the concentration of the constituent in the sample fluid passing through the flow cell. A sensor disposed at the distal end of the flow cell detects transmitted light exiting from the media, and generates outputs corresponding to a spectrum of the transmitted light. A processor communicably coupled to the sensor, captures the outputs from the sensor, and compares the incident light spectrum to the transmitted light spectrum to generate an absorbance spectrum. The processor uses the absorbance spectrum to calculate the concentration in the nanostructures, which is then used with the predetermined multiple to calculate the sample concentration.

In another aspect of the invention, a method is provided for optically determining concentration of a constituent of a sample fluid in real time. The method includes conveying the sample fluid from a proximal end to a distal end of a flow cell, and emitting, with a light source disposed in optical communication with the proximal end of the flow cell, incident light of an incident light spectrum into the flow cell. The flow cell includes media therein, which supports nanostructures that are substantially transparent in at least a portion of the incident light spectrum. The nanostructures adsorb or absorb the constituent to attain a concentration that is a predetermined multiple of a sample concentration of the constituent in the sample fluid passing through the flow cell. The method further includes detecting, with a sensor disposed at the distal end of the flow cell, transmitted light exiting from the media, and generating outputs corresponding to a spectrum of the transmitted light. A processor captures the outputs from the sensor, and compares the incident light spectrum to the transmitted light spectrum to generate an absorbance spectrum. The processor then uses the absorbance spectrum to calculate the concentration within the nanostructures, and calculates the sample concentration using this concentration and the predetermined multiple.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

The present invention is illustrated by way of example and not limitation in the figures of the accompanying drawings, in which like references indicate similar elements and in which.

DETAILED DESCRIPTION

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. In addition, well-known structures, circuits and techniques have not been shown in detail in order not to obscure the understanding of this description. The following detailed description is, therefore, not to be taken in a limiting sense, and the scope of the present invention is defined by the appended claims and their equivalents.

As used in the specification and in the appended claims, the singular forms "a", "an", and "the" include plural referents unless the context clearly indicates otherwise. For example, reference to "a sensor" includes a plurality of such sensors. In another example, reference to "an analysis" includes a plurality of such analyses.

Although specific terms are employed herein, they are used in a generic and descriptive sense only and not for purposes of limitation. All terms, including technical and scientific terms, as used herein, have the same meaning as commonly understood by one of ordinary skill in the art to which this invention belongs unless a term has been otherwise defined. It will be further understood that terms, such as those defined in commonly used dictionaries, should be interpreted as having a meaning as commonly understood by a person having ordinary skill in the art to which this invention belongs. It will be further understood that terms, such as those defined in commonly used dictionaries, should be interpreted as having a meaning that is consistent with their meaning in the context of the relevant art and the present disclosure. Such commonly used terms will not be interpreted in an idealized or overly formal sense unless the disclosure herein expressly so defines otherwise.

TERMINOLOGY

As used herein, the term "processor" and/or "computer" is meant to encompass a workstation, personal computer, personal digital assistant (PDA), wireless telephone, or any other suitable computing device including one or more integrated circuits or similar hardware computing devices, which may include a computer readable medium upon which computer readable program code (including instructions and/or data) may be disposed, with or without a user interface. Moreover, various processor and/or computer-related entities may be localized on one computer and/or distributed between two or more computers. The terms "real-time" and "on-demand" refer to sensing and responding to external events nearly simultaneously (e.g., within milliseconds or microseconds) with their occurrence, or without intentional delay, given the processing limitations of the system and the time required to accurately respond to the inputs.

Programming Languages

The system and method embodying the present invention can be programmed in any suitable language and technology, such as, but not limited to: Assembly Languages, C, C++; Visual Basic; Java; VBScript; Jscript; Node.js; BCMAscript; DHTM1; XML and CGI.

Alternative versions may be developed using other programming languages including, Hypertext Markup Language (HTML), Active ServerPages (ASP) and Javascript. Any suitable database technology can be employed, such as, but not limited to, Microsoft SQL Server or IBM AS 400.

Referring now to the Figures, embodiments of the present invention will be described.

The present inventor has recognized that measuring a constituent such as moisture within a fluid by conventional absorbance spectroscopy, e.g., by measuring the absorbance of light by the fluid at 1.4, 1.9, 2.7 μm and other wavelengths is challenging, in part, due to the need for relatively long optical paths to detect relatively low concentrations. For example, a multiple reflections flow cell may be used to lengthen the optical path to facilitate measurement of relatively low moisture concentrations.

According to the Beer-Lambert law, the amount of light absorbed by a gas is proportional to the amount of the gas in the light's path. The Beer-Lambert law may be more generally applied to fluids, e.g., gases and liquids, to measure the amount of a constituent, such as water, within a sample fluid.

Spectrophotometers, which operate on the basis of absorption spectroscopy in accordance with the Beer-Lambert law, apply light at a relatively broad range of wavelengths to a sample fluid, and measure the amount of light absorbed at specific wavelengths. Since constituents such as water absorb light at known wavelengths, the amount of light absorbed at these known wavelengths correlates to the amount of the constituents the sample fluid. Indeed, those skilled in the art will recognize that electromagnetic radiation absorption, using visible light as a specific example, includes applying a white beam source—emitting incident light of multiple wavelengths—on a sample. Upon striking the sample, photons that match the energy gap of the molecules present are absorbed and excite the molecule. Other photons transmit through the sample unaffected. By comparing the attenuation of the transmitted light with the incident light, an absorption spectrum can be obtained. An exemplary system for generating such spectrophotometric analysis is the OMA-300 Analyzer including the nova II™ UV-Vis/SW-NIR Spectrophotometer, commercially available from Applied Analytics, Inc. (Burlington, Mass.).

Figure 1A:
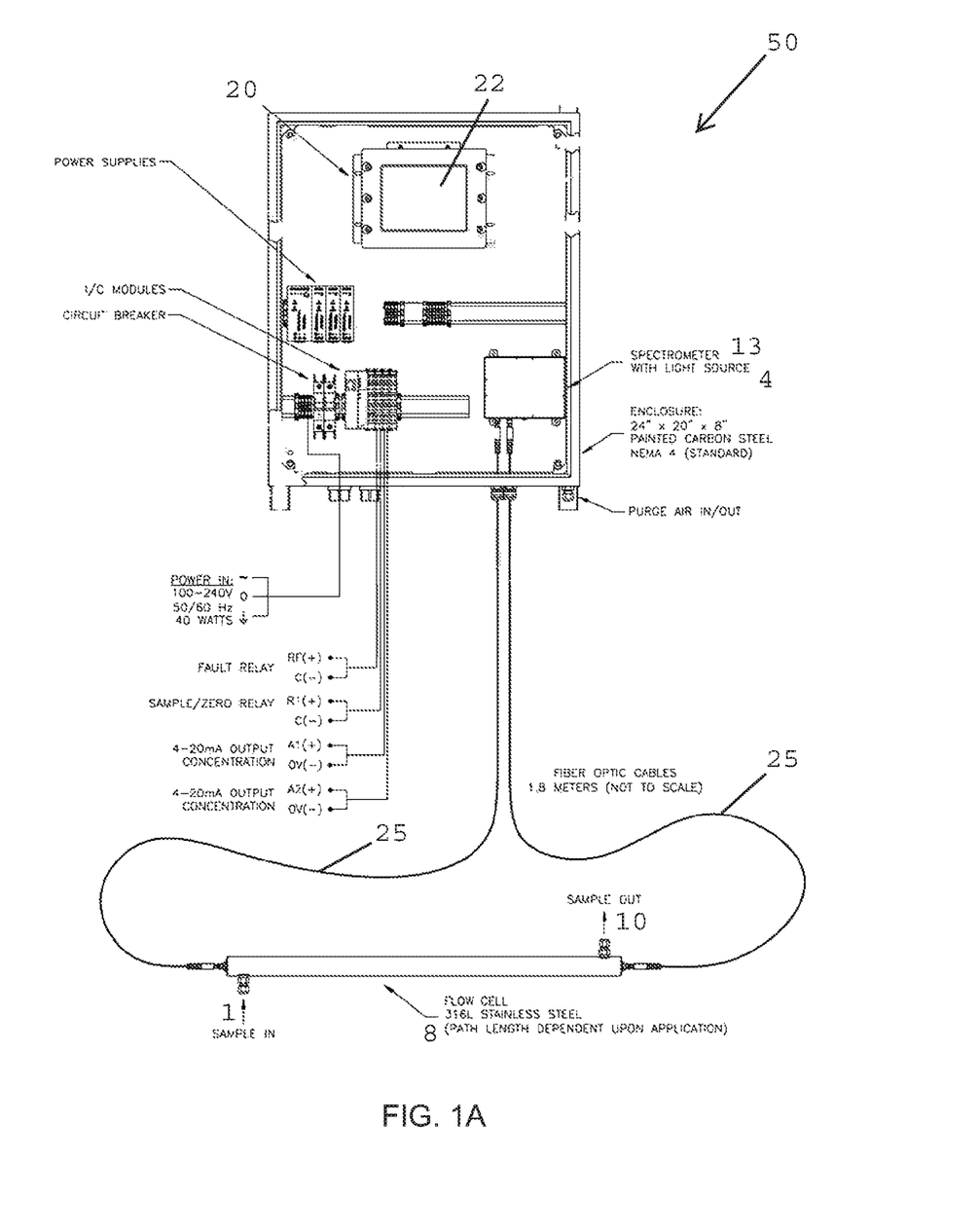
FIG. 1A is an elevational view, with portions broken away, of an embodiment of the present invention.

Referring now to FIG. 1A, in particular embodiments of the present invention, a sensor system 50 includes components of the aforementioned OMA-300 Analyzer modified to include a flow cell 8 in accordance with the inventive teachings hereof. Flow cell 8 includes an optical path fabricated from a porous media 9 which supports a nanostructures 23, as shown and described in greater detail hereinbelow with respect to FIG. 1B. In particular embodiments, media 9 is fabricated from silica, optionally with surface coating enhancements, and includes a hydrophilic nanostructures 23. As shown, conventional components of the OMA-300 usable in these embodiments include a processor 20 with an HMI (Human Machine Interface) 22, e.g., display screen/buttons, communicably coupled to a sensor 13 with integral light source 4. In particular embodiments, the combination of sensor 13 and light source 4 take the form of a spectrometer such as the aforementioned nova II™ UV-Vis/SW-NIR Spectrophotometer (Applied Analytics, Inc.). Sensor 13 is connected by fiber optic light guides 25 to flow cell 8. Flow cell 8 includes sample input and output ports 1 and 10, respectively.

Initially, it should be noted that embodiments of the present invention may be used for the detection of substantially any constituent or analyte of interest within a sample fluid (e.g., gas, liquid, or combination). Examples of detectable constituents include, but are not limited to, those in Table I below. However, for ease of explication, embodiments of the present invention will be shown and described hereinbelow with respect to moisture detection.

TABLE I acetonitrile
ammonia|NH3
aromatic hydrocarbons|BTX
benzene|C6H6
carbon dioxide|CO2
carbon disulfide|CS2
carbon monoxide|CO
carbonyl sulfide|COS
chlorine|Cl2

TABLE I-continued chlorine dioxide|ClO2
color|APHA, Saybolt . . .
copper ions|Cu2+
Diesel
dimethyl sulfide|DMS
ethanol|C2H6O
ethylene|C2H4
ferric chloride|FeCl3
fluorine|F2
glycols
hydrogen peroxide|H2O2
hydrogen sulfide|H2S
incoming materials
iron ions|Fe2+
MEG (ethylene glycol)
MEHQ (mono methyl ether hydroquinone)
mercaptans|R-SH
metal ions
methanethiol|MeSH
methane equivalency|CH4
methyl iodide|CH3I
nickel ions|Ni2+
nitric oxide|NO
nitrogen dioxide|NO2
nitrogen oxides|NOX
nitrogen trichloride|NCl3
oil in water (petroleum)
olefins
oxazoles
ozone|O3
phenol|C6H5OH
sodium hydroxide|NaOH
sulfide|S2-
sulfur dioxide|SO2
sulfur (total)
TBC (4-tert-Butylcatechol)
titanium tetrachloride|TiCl4
toluene|C7H8
transmittance
vanadium ions
vanadium oxytrichloride|VOCl3
water|H2O
Wobbe Index
xylene|C8H10

The present inventor has recognized that the amount of water accumulated in the hydrophilic nanostructures 23 supported within the media 9 is directly proportional to the amount of moisture contained in the sample passing into the media 9. The inventor further recognized that the concentration of moisture in the nanostructures 23 is significantly (e.g., many times) greater than the concentration in the sample, thus providing an optical cross section of water that can be easily detected optically, even when moisture concentration in the sample is relatively low. This easily detected moisture concentration then may be correlated to the gas phase. This use of media 9 and nanostructures 23 thus effectively amplifies the concentration of the constituent of interest (e.g., water), to facilitate detection of relatively small constituent concentrations without the need for flow cells with relatively long/multiple reflections optical paths.

Figures 1B, 2:
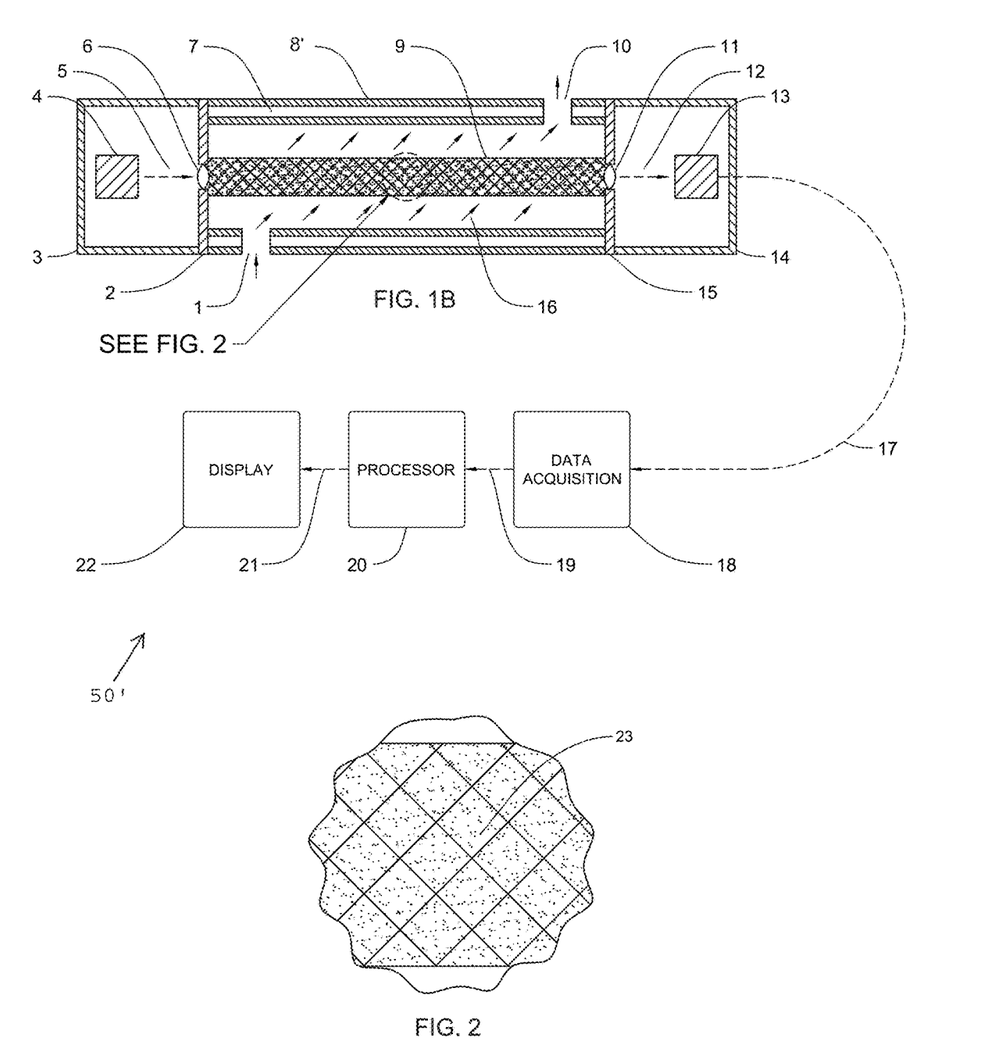
FIG. 1B, is a cross-sectional schematic view, with portions broken away, of an alternate embodiment of the present invention.
FIG. 2 is an enlarged view of a portion of the embodiment of FIG. 1B.

Referring now to FIG. 1B, aspects of the invention are shown in greater detail with respect to a sensor system 50' which is substantially similar to system 50 but for the form factor, in which flow cell 8' is housed integrally with light source 4 and sensor 13.

As shown, flow cell 8' has an input port 1 and an output port 10 through which a moisture-containing sample fluid respectively enters and exits. The sample passes into the porous media 9, which as best shown in FIG. 2, includes a porous matrix supporting a hydrophilic nanostructures 23 therein. Turning back to FIG. 1B, as the sample fluid passes through media 9, moisture is removed from the sample and retained within the nanostructures 23. The moisture depleted sample then exits from flow cell 8 via exit port 10.

In particular embodiments, the media 9 takes the form of a 15 micron silica mesh, i.e., a mesh provided with a substantially 15 micron pore size which is large enough to pass the sample fluid therethrough, while being small enough to substantially prevent the nanostructures 23 from being pushed out of the mesh during operation. Particular embodiments use pore sizes of 5 to 50 microns, while other embodiments use pore sizes of 10 to 40 microns, and 10 to 25 microns, respectively. Examples of nanostructures 23 usable in many moisture sensing applications include ZnO nanoparticles or Upsalite ($MgCO_3$), or substantially any other water absorbing or adsorbing nanomaterial capable of increasing the quantity of water within its pores while also being substantially invisible in the optical measurement region(s) associated with the analyte of interest (e.g., 1.4, 1.9, and 2.7 μm for $H_2O$). It is also noted that in the embodiments shown and described herein, the media 9 is sized and shaped, and optionally reinforced, to maintain its structural rigidity, e.g., to support the nanostructures 23, when under the pressure of the sample fluid entering through inlet 1 and flowing through the flow cell 8, 8'. The skilled artisan should recognize, however, that although media 9 is effectively shown and described as a mesh container within which nanostructures are supported, media 9 may take substantially any form capable of providing the required support, including a surface to which nanostructures 23 are adhered, without departing from the scope of the present invention.

As mentioned above, the nanostructures 23 absorb or adsorb the constituent of interest proportionately to the presence of the constituent in the sample fluid. In particular embodiments, the media is configured to adsorb and/or absorb the constituent to attain a concentration that is a predetermined multiple of the concentration of the constituent in the sample fluid passing through the flow cell.

Referring to FIG. 1B, light 5 at a desired wavelength(s) is generated by light source 4 and passes into a proximal end of the media 9 within flow cell 8', via lens 6. In particular embodiments, light source 4 is a Tungsten light source (CST-0513) as used in the aforementioned OMA-300 from Applied Analytics, Inc. Alternatively, Xenon and/or LED light sources 4 may be used in particular applications. As shown, lens 6 is supported in a proximal end plate 2 of flow cell 8', and serves to collimate the light 5 to form a concentrated beam capable of passing through the media 9 and nanostructures 23 with sufficient intensity to be detected at a distal end thereof. As shown, once the light 5 emerges from the distal end of the media 9 and nanostructures 23, a collimator lens 11, similar to lens 6 and supported within a distal end plate 15, disperses the light at 12 for capture by sensor 13 configured to detect light in the wavelength(s) generated by light source 4. In particular embodiments, examples of sensor 13 include the nova II™ UV-Vis/SW-NIR Spectrophotometer, or alternatively, the detector may include a Fabry-Perot interferometer, such as the Model C13272 MEMS FPI near-infrared spectrum sensor with an InGaAs PIN photodiode and a MEMS-FPI tunable filter, available from Hamamatsu Photonics K.K. (Hamamatsu City, Shizuoka Pref., 430-8587, Japan), controlled by a Model 13294 evaluation board from Hamamatsu.

As also shown, data 17 captured by sensor 13 is fed to processor 20, e.g., via data acquisition module 18, where the data is formatted and forwarded to processor 20 where the amount of light absorbed by the constituent (water) is correlated to the amount of the constituent in the sample and communicated at 21 to a user via HMI 22.

In particular embodiments, the processor captures the outputs 17/19 from the sensor 13, including the spectrum of the transmitted light 12, and compares these outputs to the spectrum of the incident light 5 to generate an absorbance spectrum. The processor 20 then uses the absorbance spectrum to calculate the concentration of moisture in the nanostructures 23, e.g., using the Beer-Lambert law. The processor then calculates the sample concentration using the media concentration and the aforementioned predetermined multiple associated with the particular media. Those skilled in the art will recognize that the predetermined multiple will remain substantially constant for a particular media and constituent of interest. However, changes in the media and/or constituents may generate corresponding changes in the predetermined multiple.

In particular embodiments, processor 20 and HMI 22 include those of the aforementioned OMA-300, including the ECLIPSE™ analysis software (Applied Analytics, Inc.) which processes the raw absorbance data from the sensor 13 to visualize real-time sample absorbance and output chemical concentrations, with a touch-responsive visual interface for the operator.

As also shown, light source 4 is protected from physical damage, particulate, and optionally from moisture, by an end cap 3. Sensor 13 is similarly protected by end cap 14. When the nanomaterial/media 9, 23 becomes saturated with the constituent (e.g., water), the nanomaterial/media may be replaced or regenerated by supplying heat from a suitable heat source (not shown) into a chamber 7 within the outer walls of the flow cell 8'.

Tests to validate the foregoing were performed using a sensor 13 in the form of a Model C13272 MEMS FPI near-infrared spectrum sensor with an InGaAs PIN photodiode and a MEMS-FPI (Fabry-Perot interferometer) tunable filter, available from Hamamatsu Photonics K.K. (Hamamatsu City, Shizuoka Pref., 430-8587, Japan), controlled by a Model 13294 evaluation board from Hamamatsu. The light source 4 was a Tungsten light source (CST-0513) from Applied Analytics, Inc. (AAI) as used in the OMA-300. Additional validation tests were performed using the OMA-300 Process Analyzer with a SWNIR (Short Wave Infrared) detector and the MCP-200 Infrared Analyzer (from AAI).

Although the foregoing embodiments have been shown and described in the form of a moisture sensor, those skilled in the art should recognize that various embodiments may be used to capture any number of constituents within a fluid. Moreover, the constituents and sample fluids may take any number of phases, e.g., embodiments of the invention may be used to detect a gas within a gas, a gas within a liquid, a liquid within a liquid, etc.

Figure 3:
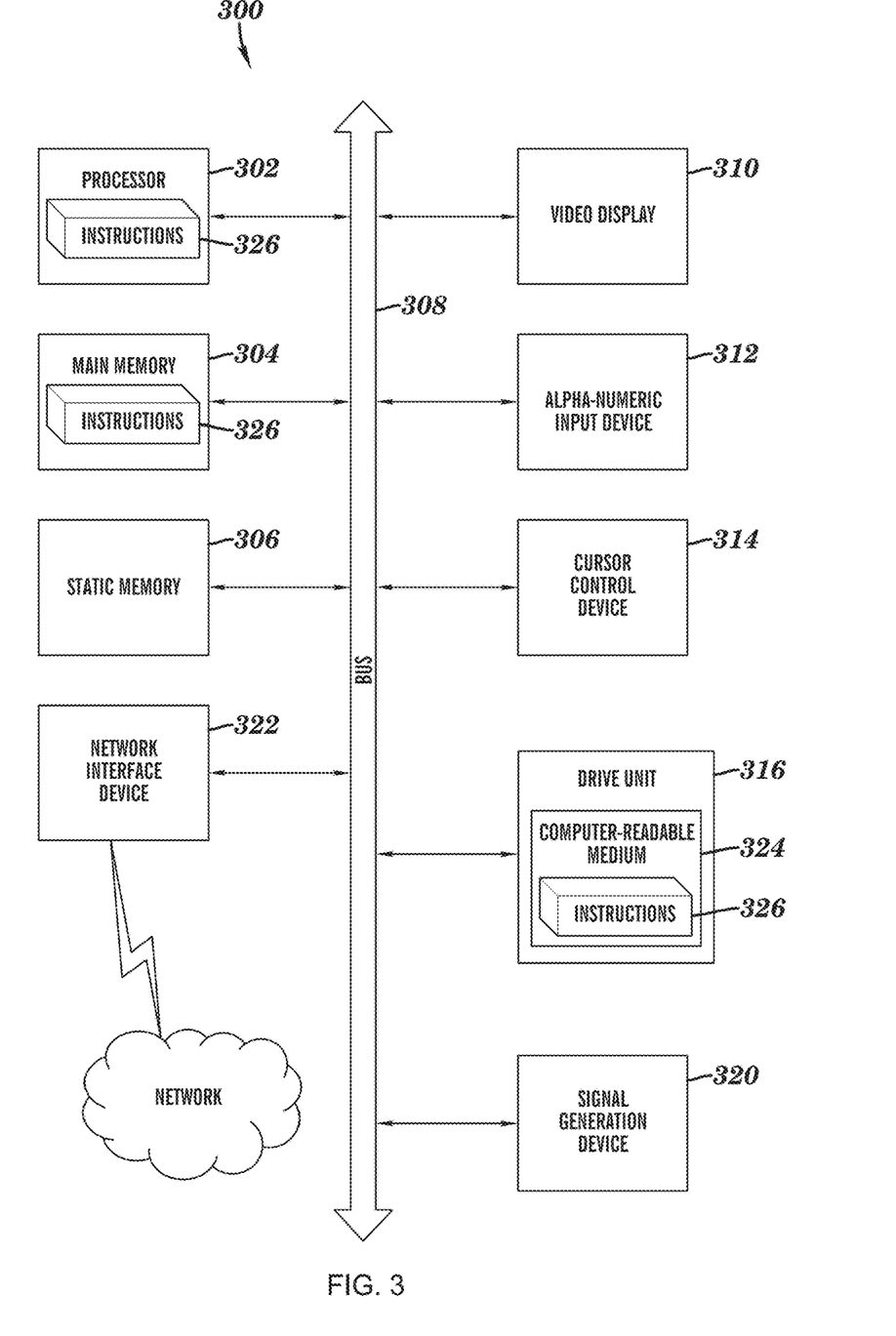
FIG. 3 is a schematic view of a computer system usable in embodiments of the present invention.

FIG. 3 shows a diagrammatic representation of a machine in the exemplary form of a computer system 300 within which a set of instructions, for causing the processor to perform any one of the methodologies discussed above, may be executed. Computer system 300 may be used in various embodiments of the present invention, e.g., as one or more of data acquisition module 18, processor 20 and/or display 22. In alternative embodiments, the machine may include a network router, a network switch, a network bridge, Personal Digital Assistant (PDA), a cellular telephone, a web appliance or any machine capable of executing a sequence of instructions that specify actions to be taken by that machine.

The computer system 300 includes a processor 302, a main memory 304 and a static memory 306, which communicate with each other via a bus 308. The computer system 300 may further include a video display unit 310 (e.g., a liquid crystal display (LCD), plasma, cathode ray tube (CRT), etc.). The computer system 300 may also include an alpha-numeric input device 312 (e.g., a keyboard or touchscreen), a cursor control device 314 (e.g., a mouse), a drive (e.g., disk, flash memory, etc.,) unit 316, a signal generation device 320 (e.g., a speaker) and a network interface device 322.

The drive unit 316 includes a computer-readable medium 324 on which is stored a set of instructions (i.e., software) 326 embodying any one, or all, of the methodologies described above. The software 326 is also shown to reside, completely or at least partially, within the main memory 304 and/or within the processor 302. The software 326 may further be transmitted or received via the network interface device 322. For the purposes of this specification, the term "computer-readable medium" shall be taken to include any medium that is capable of storing or encoding a sequence of instructions for execution by the computer and that cause the computer to perform any one of the methodologies of the present invention, and as further described hereinbelow.

The present invention has been described in particular detail with respect to various possible embodiments, and those of skill in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead performed by a single component.

Some portions of above description present the features of the present invention in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by real time network operating systems.

Embodiments of the present invention also relate to an apparatus for performing the operations herein. This apparatus may be specially constructed for the required purposes, or it may comprise a computer selectively activated or reconfigured by a computer program stored on a computer readable medium that can be accessed by the computer. Such a computer program may be stored in a tangible, non-transitory, computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), any other appropriate static, dynamic, or volatile memory or data storage devices, or other type of media suitable for storing electronic instructions, and each coupled to a computer system bus. Furthermore, the computers referred to in the specification may include a single processor or may be architectures employing multiple processor designs for increased computing capability.

Various systems may also be used with programs in accordance with the teachings herein, or it may prove convenient to construct more specialized apparatus to perform the required method steps. The required structure for a variety of these systems will be apparent to those of skill in the art, along with equivalent variations. In addition, the present invention is not described with reference to any particular programming language. It is appreciated that a variety of programming languages may be used to implement the teachings of the present invention as described herein, and any references to specific languages are provided for disclosure of enablement and best mode of the present invention.

The present invention is well suited to a wide variety of computer network systems over numerous topologies. Within this field, the configuration and management of large networks comprise storage devices and computers that are communicatively coupled to dissimilar computers and storage devices over a network, such as the Internet.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims. It should be further understood that any of the features described with respect to one of the embodiments described herein may be similarly applied to any of the other embodiments described herein without departing from the scope of the present invention.

Having thus described the invention, what is claimed is:

1. A system for optically determining concentration of a constituent of a sample fluid in real time, the system comprising:
 a flow cell configured to convey the sample fluid therethrough from a proximal end to a distal end;
 a light source disposed in optical communication with the proximal end of the flow cell, the light source configured to emit incident light of an incident light spectrum into the flow cell;
 media disposed within the flow cell;
 nanostructures supported by the media, the nanostructures being substantially transparent in at least a portion of the incident light spectrum, the nanostructures configured to adsorb or absorb the constituent to attain a nanostructures concentration that is a predetermined multiple of a sample concentration of the constituent in the sample fluid passing through the flow cell;
 at least one sensor disposed at the distal end of the flow cell, the sensor configured to detect transmitted light exiting from the media, and to generate one or more outputs corresponding to a transmitted light spectrum of the transmitted light;
 a processor communicably coupled to the sensor, the processor configured to capture the outputs from the sensor, and to compare the incident light spectrum to the transmitted light spectrum to generate an absorbance spectrum;
 the processor further configured to use the absorbance spectrum to calculate the nanostructures concentration, and to use the nanostructures concentration and the predetermined multiple to calculate the sample concentration.

2. The system of claim 1, wherein the processor is configured to use the Beer-Lambert law to calculate the nanostructures concentration.

3. The system of claim 1, comprising a first lens disposed between the light source and the media at the proximal end of the flow cell to guide the incident light into the media, and a second lens disposed between the media and the sensor at the distal end of the flow cell to guide the transmitted light to the sensor.

4. The system of claim 3, comprising a first fiber optic light guide disposed between the light source and the flow cell, and a second fiber optic light guide disposed between the flow cell and the sensor.

5. The system of claim 1, wherein the media is porous, having pores with sizes ranging from 5 to 50 microns.

6. The system of claim 5, wherein the media has pores with sizes ranging from 10 to 40 microns.

7. The system of claim 6, wherein the media has pores with sizes ranging from 10 to 25 microns.

8. The system of claim 1, wherein the at least one sensor comprises a spectrometer.

9. The system of claim 8, wherein the at least one sensor comprises a spectrophotometer.

10. The system of claim 1, wherein the constituent of interest is water, and the nanostructures is hydrophilic.

11. A method for optically determining concentration of a constituent of a sample fluid in real time, the method comprising:
 (a) conveying the sample fluid from a proximal end to a distal end of a flow cell;
 (b) emitting, with a light source disposed in optical communication with the proximal end of the flow cell, incident light of an incident light spectrum into the flow cell,
 the flow cell including media therein, and
 nanostructures supported by the media, the nanostructures being substantially transparent in at least a portion of the incident light spectrum, the nanostructures configured to adsorb or absorb the constituent to attain a nanostructures concentration that is a predetermined multiple of a sample concentration of the constituent in the sample fluid passing through the flow cell;
 (c) detecting, with at least one sensor disposed at the distal end of the flow cell, transmitted light exiting from the media;
 (d) generating one or more outputs corresponding to a transmitted light spectrum of the transmitted light;

(e) capturing, with a processor communicably coupled to the sensor, the outputs from the sensor, and
(f) comparing, with the processor, the incident light spectrum to the transmitted light spectrum to generate an absorbance spectrum;
(g) calculating, with the processor, the nanostructures concentration using the absorbance spectrum, and
(h) calculating, with the processor, the sample concentration using the nanostructures concentration and the predetermined multiple.

12. The method of claim 11, wherein said calculating (g) further comprises using the Beer-Lambert law.

13. The method of claim 11, comprising guiding the incident light into the media with a first lens disposed between the light source and the media at the proximal end of the flow cell, and guiding the transmitted light to the sensor with a second lens disposed between the media and the sensor at the distal end of the flow cell.

14. The method of claim 13, comprising disposing a first fiber optic light guide between the light source and the flow cell, and a second fiber optic light guide between the flow cell and the sensor.

15. The method of claim 11, wherein the media is porous, having pores with sizes ranging from 5 to 50 microns.

16. The method of claim 15, wherein the media has pores with sizes ranging from 10 to 40 microns.

17. The method of claim 16, wherein the media has pores with sizes ranging from 10 to 25 microns.

18. The method of claim 11, wherein the at least one sensor comprises a spectrometer.

19. The method of claim 18, wherein the at least one sensor comprises a photospectrometer.

20. The method of claim 19, wherein the constituent of interest is water, and the nanostructures is hydrophilic.

* * * * *